US012582465B2

(12) United States Patent
Henchie et al.

(10) Patent No.: US 12,582,465 B2
(45) Date of Patent: Mar. 24, 2026

(54) TISSUE RESURFACING DEVICES AND METHODS THEREOF

(71) Applicant: BOSTON SCIENTIFIC SCIMED, INC., Maple Grove, MN (US)

(72) Inventors: Travis Henchie, Worcester, MA (US); Joseph W. King, Franklin, MA (US); John T. Favreau, Spencer, MA (US); Lauren Sfakis Lydecker, Millbury, MA (US); Amanda L Smith, Boston, MA (US); Andrew Pic, Northboro, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 992 days.

(21) Appl. No.: 17/672,148

(22) Filed: Feb. 15, 2022

(65) Prior Publication Data

US 2022/0257317 A1 Aug. 18, 2022

Related U.S. Application Data

(60) Provisional application No. 63/149,844, filed on Feb. 16, 2021.

(51) Int. Cl.
 *A61B 18/14* (2006.01)
 *A61F 2/07* (2013.01)
 *A61B 18/00* (2006.01)

(52) U.S. Cl.
 CPC ............ *A61B 18/1492* (2013.01); *A61F 2/07* (2013.01); *A61B 2018/00202* (2013.01); *A61B 2018/0022* (2013.01); *A61B 2018/00577* (2013.01); *A61B 2018/00613* (2013.01); *A61B 2018/1415* (2013.01); *A61F 2210/0014* (2013.01)

(58) Field of Classification Search
 CPC ...... A61B 18/1492; A61B 2018/00202; A61B 2018/0022; A61B 2018/00244; A61B 2018/00267; A61B 2018/00494; A61B 2018/00577; A61B 2018/00613; A61B 2018/1415; A61F 2/07; A61F 2210/0014
 See application file for complete search history.

(56) References Cited

U.S. PATENT DOCUMENTS

| | | |
|---|---|---|
| 5,176,693 A | 1/1993 | Pannek, Jr. |
| 5,196,024 A | 3/1993 | Barath |

(Continued)

FOREIGN PATENT DOCUMENTS

EP 3730081 A1 10/2020

OTHER PUBLICATIONS

International Search Report and Written Opinion dated May 12, 2022 for International Application No. PCT/US2022/016433.

*Primary Examiner* — Tigist S Demie
(74) *Attorney, Agent, or Firm* — Seager, Tufte & Wickhem, LLP

(57) ABSTRACT

A resurfacing device for removing a thin layer of diseased tissue while minimizing damage to the underlying tissue layers may include an expandable scaffold attached to a catheter shaft, at least one electrode disposed on the expandable scaffold, and a plurality of debridement elements disposed on an outer surface of the expandable scaffold. The expandable scaffold is positioned in apposition to the target tissue, the scaffold is expanded and the electrodes are activated to ablate diseased tissue. The scaffold is rotated to remove the ablated tissue.

18 Claims, 6 Drawing Sheets

(56) References Cited

U.S. PATENT DOCUMENTS

| | | | |
|---|---|---|---|
| 5,320,634 A | 6/1994 | Vigil et al. | |
| 5,336,234 A | 8/1994 | Vigil et al. | |
| 5,616,149 A | 4/1997 | Barath | |
| 5,649,953 A | 7/1997 | Lefebvre | |
| 5,797,935 A | 8/1998 | Barath | |
| 6,500,186 B2 | 12/2002 | Lafontaine et al. | |
| 6,562,062 B2 | 5/2003 | Jenusaitis et al. | |
| 6,632,231 B2 | 10/2003 | Radisch | |
| 6,746,463 B1 | 6/2004 | Schwartz | |
| 6,808,531 B2 | 10/2004 | Lafontaine et al. | |
| 6,951,566 B2 | 10/2005 | Lary | |
| 7,011,670 B2 | 3/2006 | Radisch, Jr. | |
| 7,029,483 B2 | 4/2006 | Schwartz | |
| 7,131,981 B2 | 11/2006 | Appling et al. | |
| 7,153,315 B2 | 12/2006 | Miller | |
| 7,172,609 B2 | 2/2007 | Radisch, Jr. | |
| 7,270,673 B2 | 9/2007 | Yee et al. | |
| 7,303,572 B2 | 12/2007 | Melsheimer et al. | |
| 7,338,463 B2 | 3/2008 | Vigil | |
| 7,396,358 B2 | 7/2008 | Appling et al. | |
| 7,413,558 B2 | 8/2008 | Kelley et al. | |
| 7,416,555 B2 * | 8/2008 | Krivoruchko .. | A61B 17/320758 606/159 |
| 7,494,497 B2 | 2/2009 | Weber | |
| 7,658,744 B2 | 2/2010 | Jackson | |
| 7,691,119 B2 | 4/2010 | Farnan | |
| 7,753,907 B2 | 7/2010 | Dimatteo et al. | |
| 7,758,604 B2 | 7/2010 | Wu et al. | |
| 7,799,043 B2 | 9/2010 | O'Brien et al. | |
| 7,879,053 B2 | 2/2011 | Trinidad | |
| 7,993,358 B2 | 8/2011 | O'Brien | |
| 8,048,093 B2 | 11/2011 | Mapes et al. | |
| 8,066,726 B2 | 11/2011 | Kelley | |
| 8,211,354 B2 | 7/2012 | Burton | |
| 8,454,637 B2 | 6/2013 | Aggerholm et al. | |
| 8,491,615 B2 | 7/2013 | Manderfeld et al. | |
| 8,715,334 B2 | 5/2014 | Clerc et al. | |
| 8,870,816 B2 | 10/2014 | Chambers et al. | |
| 9,095,688 B2 | 8/2015 | Burton | |
| 9,179,936 B2 | 11/2015 | Feld et al. | |
| 9,199,066 B2 | 12/2015 | Konstantino et al. | |
| 9,211,394 B2 | 12/2015 | Leffel | |
| 9,216,033 B2 | 12/2015 | Feld et al. | |
| 9,302,071 B2 | 4/2016 | Manderfeld et al. | |
| 9,364,255 B2 | 6/2016 | Weber | |
| 9,375,328 B2 | 6/2016 | Farnan | |
| 9,439,790 B2 | 9/2016 | Clerc et al. | |
| 9,604,036 B2 | 3/2017 | Burton et al. | |
| 9,757,535 B2 | 9/2017 | Rajagopalan et al. | |
| 9,763,691 B2 | 9/2017 | Spencer et al. | |
| 9,993,281 B2 | 6/2018 | Kelly et al. | |
| 10,117,759 B2 | 11/2018 | Jordan et al. | |
| 10,117,761 B2 | 11/2018 | O'Shaughnessy et al. | |
| 10,299,857 B2 | 5/2019 | Rajagopalan et al. | |
| 10,342,684 B2 | 7/2019 | Firstenberg et al. | |
| 10,441,406 B2 | 10/2019 | Firstenberg et al. | |
| 10,575,904 B1 | 3/2020 | Ben Oren et al. | |
| 2003/0163148 A1 | 8/2003 | Wang et al. | |
| 2005/0070888 A1 | 3/2005 | Dimatteo et al. | |
| 2005/0119678 A1 | 6/2005 | O'Brien et al. | |
| 2005/0137615 A1 | 6/2005 | Mapes et al. | |
| 2005/0149102 A1 | 7/2005 | Radisch et al. | |
| 2005/0288629 A1 | 12/2005 | Kunis | |
| 2006/0111736 A1 | 5/2006 | Kelley | |
| 2006/0116700 A1 | 6/2006 | Crow | |
| 2006/0116701 A1 | 6/2006 | Crow | |
| 2006/0129093 A1 | 6/2006 | Jackson | |
| 2006/0135980 A1 | 6/2006 | Trinidad | |
| 2006/0247674 A1 | 11/2006 | Roman | |
| 2007/0016232 A1 | 1/2007 | St.Martin et al. | |
| 2007/0060863 A1 | 3/2007 | Goeken et al. | |
| 2007/0213752 A1 | 9/2007 | Goodin et al. | |
| 2009/0287137 A1 | 11/2009 | Crowley | |
| 2013/0041391 A1 * | 2/2013 | Spencer ........ | A61B 17/320725 606/159 |
| 2013/0345670 A1 | 12/2013 | Rajagopalan et al. | |
| 2015/0141987 A1 | 5/2015 | Caplan et al. | |
| 2015/0148738 A1 | 5/2015 | Caplan et al. | |
| 2015/0223866 A1 * | 8/2015 | Buelna ............... | A61B 18/1492 606/41 |
| 2019/0254740 A1 * | 8/2019 | Koya ..................... | A61N 1/327 |
| 2019/0262031 A1 | 8/2019 | Efremkin | |
| 2019/0307992 A1 | 10/2019 | Haverkost et al. | |
| 2019/0350567 A1 | 11/2019 | Cummins et al. | |
| 2019/0388133 A1 | 12/2019 | Sharma | |
| 2020/0060758 A1 | 2/2020 | Rajagopalan et al. | |
| 2020/0060942 A1 | 2/2020 | Rajagopalan et al. | |
| 2020/0155218 A1 | 5/2020 | Pasricha et al. | |
| 2020/0253659 A1 | 8/2020 | Lee et al. | |

* cited by examiner

TISSUE RESURFACING DEVICES AND METHODS THEREOF

CROSS REFERENCE TO RELATED APPLICATIONS

This application claims the benefit of and priority to U.S. Provisional Patent Application Ser. No. 63/149,844 filed on Feb. 16, 2021, the disclosure of which is incorporated herein by reference.

TECHNICAL FIELD

The present disclosure pertains to medical devices, and methods for manufacturing medical devices. More particularly, the present disclosure pertains to tissue ablation medical devices and methods for manufacturing and using such devices.

BACKGROUND

The cell types in the intestinal lining play a key role in the absorption of nutrients. Differences in absorption across the intestinal tract can play a role in many diseases including diabetes and metabolic disorders. Recent clinical evidence suggests that duodenal metaplasia (change in endothelial cell type within the duodenum), resulting from high sugar and fat diets may cause insulin resistance within the tissue, potentially resulting in type II diabetes. One approach to addressing duodenal metaplasia is the ablation or removal of diseased duodenal mucosal tissue. Removal of metaplastic tissue may allow for healthy endothelium to repopulate the duodenum and resume normal metabolism. There is an ongoing need to provide alternative medical devices for tissue ablation, as well as alternative methods for manufacturing and using medical devices.

BRIEF SUMMARY

This disclosure provides design, material, manufacturing method, and use alternatives for medical devices. An example medical device includes a resurfacing device comprising a catheter shaft, an expandable scaffold attached to the catheter shaft, at least one electrode disposed on the expandable scaffold, and a plurality of debridement elements disposed on an outer surface of the expandable scaffold.

Alternatively or additionally to the embodiment above, the scaffold is self-expandable.

Alternatively or additionally to the embodiment above, the scaffold is a shape memory stent.

Alternatively or additionally to the embodiment above, the scaffold is a balloon.

Alternatively or additionally to the embodiment above, the debridement elements are elongate members each having a first end attached to the scaffold, and a second, free end extending radially away from the scaffold.

Alternatively or additionally to the embodiment above, the elongate members are metal blades.

Alternatively or additionally to the embodiment above, the debridement elements include a micropattern of projections extending radially away from the outer surface of the scaffold.

Alternatively or additionally to the embodiment above, the at least one electrode includes at least first and second electrodes aligned longitudinally along a single axis along the scaffold.

Alternatively or additionally to the embodiment above, the at least one electrode includes at least first and second electrodes aligned circumferentially around the scaffold.

Alternatively or additionally to the embodiment above, the at least one electrode is a radiofrequency electrode.

Alternatively or additionally to the embodiment above, the at least one electrode is configured for electroporation.

Alternatively or additionally to the embodiment above, the scaffold and debridement elements are a monolithic structure.

Alternatively or additionally to the embodiment above, the debridement elements are fixed to the scaffold.

Another example resurfacing device comprises a catheter shaft, a self-expandable shape memory scaffold attached to the catheter shaft, at least one radiofrequency electrode disposed on the scaffold, and a plurality of debridement elements disposed on an outer surface of the scaffold.

Alternatively or additionally to the embodiment above, the debridement elements are elongate members each having a first end attached to the scaffold, and a second, free end extending radially away from the scaffold.

Alternatively or additionally to the embodiment above, the elongate members are metal blades.

Alternatively or additionally to the embodiment above, the debridement elements include a micropattern of projections extending radially away from the outer surface of the scaffold.

Alternatively or additionally to the embodiment above, the scaffold and debridement elements are a monolithic structure.

Alternatively or additionally to the embodiment above, the debridement elements are fixed to the scaffold.

An example method of resurfacing tissue comprises advancing an expandable resurfacing device into contact with tissue at a treatment target site in an unexpanded configuration, the resurfacing device comprising a catheter shaft, an expandable scaffold attached to the catheter shaft, at least one electrode disposed on the expandable scaffold, and a plurality of debridement elements disposed on an outer surface of the expandable scaffold. The method further comprises expanding the scaffold, activating the at least one electrode to ablate tissue, and rotating and withdrawing the scaffold from the target site to remove the ablated tissue.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
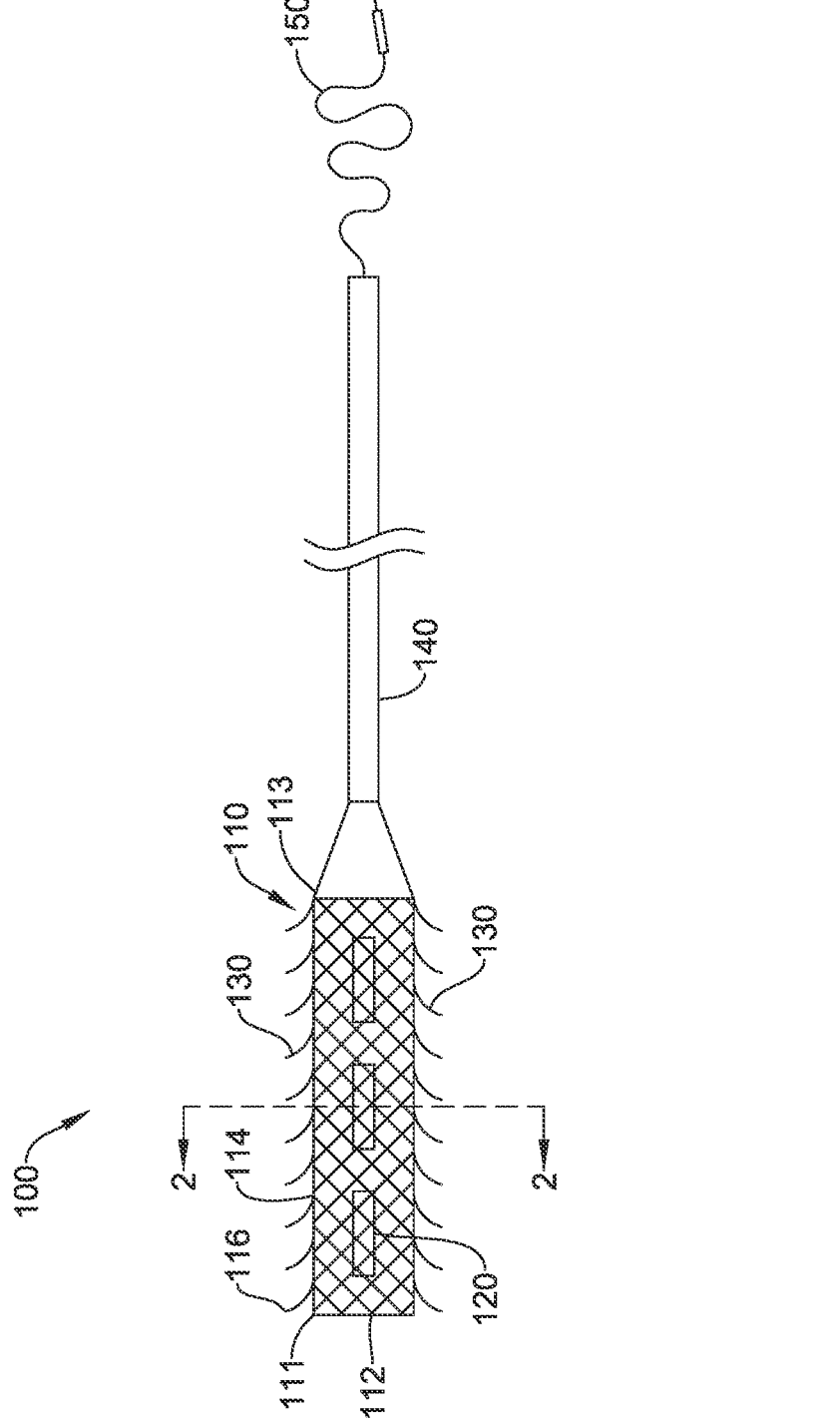
FIG. 1 is a side view of an illustrative resurfacing device.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

The mucosal resurfacing device provides an approach for removal of metaplastic endothelial tissue from the duodenum while minimizing damage to the underlying submucosal layers to treat type II diabetes. The resurfacing device incorporates radiofrequency ablation (RFA) and/or irreversible electroporation (IRE) in conjunction with debridement capabilities.

The purpose of the resurfacing device is to first ablate a thin layer of tissue and then debride the burned tissue, leaving healthy tissue to regrow and heal the treated area as part of duodenal mucosal resurfacing (DMR) procedures. Ablating a shallow layer of tissue provides a transitional zone of healthy and necrotic tissue, that when scraped is removed easily as is currently carried out during RFA debridement treatments of occluded stents. The electrode geometry and generator settings may be varied to achieve a controlled tissue ablation depth, which in turn provides control over the depth of mucosal resurfacing required. This has an added advantage over current resurfacing techniques where very little control is achievable. In addition to its use in the duodenum, the present invention may be used in any bodily vessel, such as in the esophagus, trachea, bronchi, colon, biliary tract, urinary tract, prostate, as well as in a variety of other applications in the body.

FIG. 1 illustrates a resurfacing device 100 with an expandable scaffold 110 attached to a catheter shaft 140. The expandable scaffold 110 may have the structure of an expandable stent having a plurality of filaments 112. The expandable scaffold 110 may be self-expandable or it may be expanded using a balloon. The expandable scaffold 110 may include one or more electrodes 120 and a plurality of debridement elements 130, such as the elongate blades illustrated in FIG. 1. An electrical connection 150 may extend from the electrodes 120 through the interior of the expandable scaffold 110 and through the lumen of the catheter shaft 140 to a power source located proximal of the catheter shaft 140.

Embodiments of the expandable scaffold 110 include stents having a constant diameter as illustrated in FIG. 1. In other examples, the expandable scaffold 110 may have one or more tapers, flares and/or other changes in diameter in the body and/or at an end. In some examples, the expandable scaffold 110 may have a basket structure. The shape of the expandable scaffold 110 may be selected to provide a desired amount of surface area to be in contact with the tissue to be resurfaced. The expandable scaffold 110 may be formed from a plurality of strands or filaments 112 that are woven, knitted, twisted, or braided into a tubular structure. In other examples, the expandable scaffold 110 may be formed from a single piece solid tube that is laser cut to form a lattice type structure of struts 112. The expandable scaffold 110 may be formed from shape memory metal, including super-elastic metals, such as nitinol, or polymers such as polytetrafluoroethylene (PTFE).

At least one electrode 120 is disposed on the outer surface of the expandable scaffold 110. The electrode 120 may be configured to deliver radiofrequency ablation (RFA) and/or irreversible electroporation (IRE) energy. For bipolar RFA/IRE, adjacent electrodes 120 may be positioned adjacent one another to provide a desired ablation profile. In some examples, a plurality of electrodes 120 are aligned circumferentially around the scaffold 110. The electrodes 120 may be provided in a single circumferential ring or in a plurality of circumferential rings. In other examples, the electrodes 120 may be disposed in a staggered arrangement or they may spiral helically around the scaffold 110. For monopolar applications, a plurality of electrodes 120 may be disposed longitudinally along a single axis along the scaffold 110, as shown in FIG. 1.

The outer surface of the expandable scaffold 110 may include a plurality of debridement elements 130. The debridement elements 130 may be formed monolithically with the scaffold 110, such as by cutting, etching, or molding. In other examples, the debridement elements 130 may be attached to the scaffold 110 such as by soldering, welding, with adhesive, or any other suitable connection. The debridement elements 130 may extend radially outward from the outer surface of the expandable scaffold 110 and be configured to remove ablated tissue when the scaffold 110 is rotated and/or moved axially against the ablated tissue. The debridement elements 130 may extend radially outward from the outer surface of the scaffold by 1-700 μm.

In some examples, the debridement elements 130 may be elongate elements with a first end 114 attached to or formed with the scaffold 110, and a second end 116 that extends radially away from the scaffold and is free from any attachment to the scaffold 110, as illustrated in FIG. 1. In the example illustrated in FIG. 1, the second end 116 of each debridement element 130 extends toward the distal end 111 of the scaffold 110. This orientation may provide the advantage of allowing for easier proximal withdrawal of the scaffold 110 into an outer sheath 160 (see FIG. 3) for removal of the device 100 from the body. In other examples, the direction may be reversed, with the second end 116 of each debridement element 130 extending towards the proximal end 113 of the scaffold 110. In other examples, the debridement elements 130 may have varied orientations, with some free ends 116 facing proximal and some facing distal. Still other debridement elements 130 may be oriented circumferentially, extending transverse to the longitudinal axis of the scaffold 110.

The elongate elements may be metal blades and may have sharpened side edges. In other examples, the elongate debridement elements 130 may have blunt or non-sharp side edges. The elongate elements may be made of shape memory material and may be heat set and biased at a desired pre-determined angle relative to the outer surface of the scaffold 110. The angle may be between 5 degrees and 90 degrees. In some examples, the angle may be between 10 degrees and 45 degrees. The resurfacing device 100 may be delivered inside an outer sheath 160 in a compressed configuration in which the scaffold 110 is held in a compressed configuration with the debridement elements 130 held against the outer surface of the scaffold. The outer sheath 160 may protect tissue from the debridement elements 130 and hold the debridement elements 130 in a compressed configuration until the device is in the desired position. When the outer sheath 160 is removed, the scaffold 110 expands and the debridement elements 130 return to their biased, extended configuration.

Figure 2:
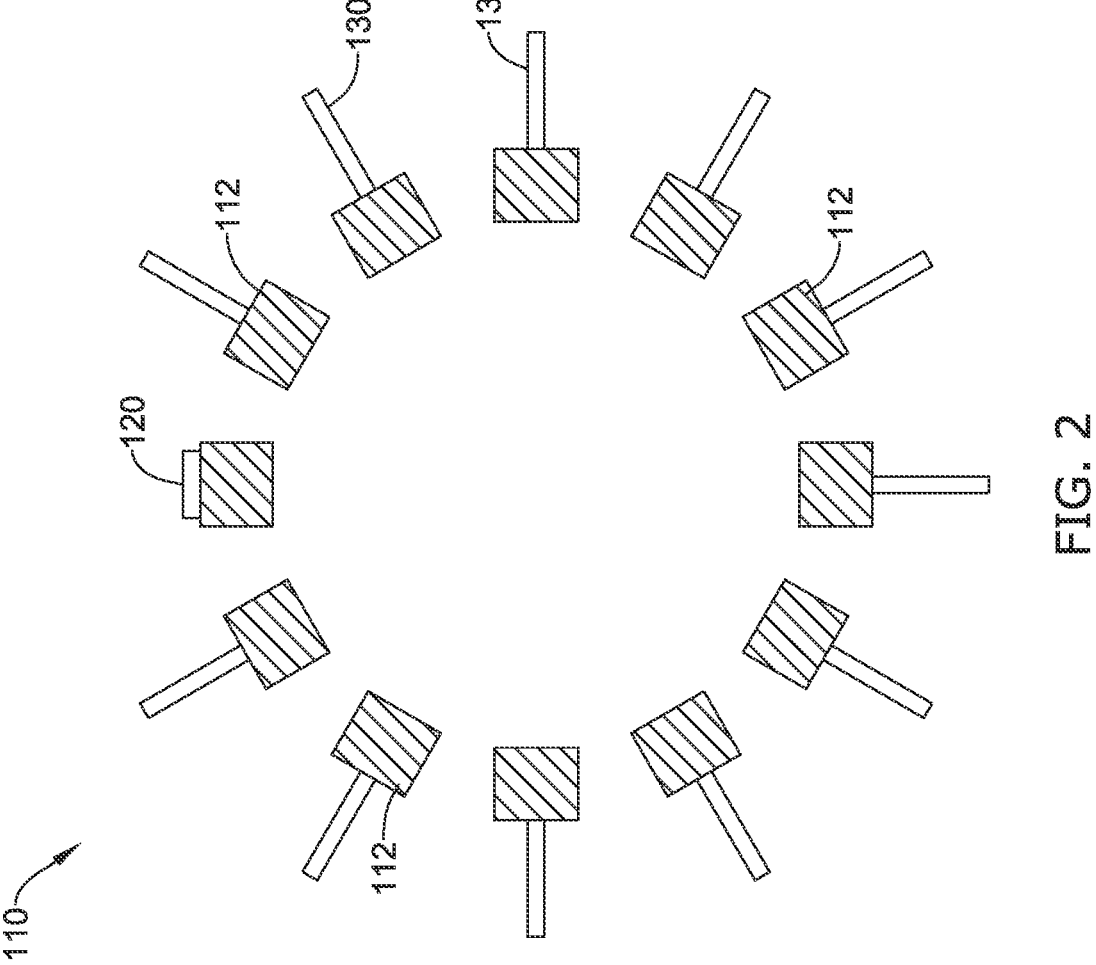
FIG. 2 is a cross-sectional view of the resurfacing device of FIG. 1 taken along line 2-2.

In the cross-sectional view shown in FIG. 2, elongate debridement elements 130 are shown extending radially outward from the outer surface of the struts or filaments 112 of the scaffold 110. The electrode 120 is also seen disposed on the outer surface of the strut or filament 112. In some examples, the debridement elements 130 may be disposed circumferentially around the scaffold 110, as shown in FIG. 2. In other examples, the debridement elements 130 may be disposed on only half or a fraction of the outer circumference of the scaffold 110.

In one example, the debridement elements 130 may be cut from the filaments 112 forming the stent, such as the "quills" or "barbs" described in U.S. Pat. No. 8,715,334, the entire content of which is incorporated herein by reference. In another example, the debridement elements 130 may be teeth defined between grooves as described in U.S. Pat. No. 10,117,761, the entire content of which is incorporated herein by reference. In a further example, the scaffold 110 may be molded from a polymer material and the debridement elements 130 may be 3D structures molded into the outer surface of the scaffold 110 as described in U.S. Pat. No. 10,117,759, the entire content of which is incorporated herein by reference.

Figure 3:
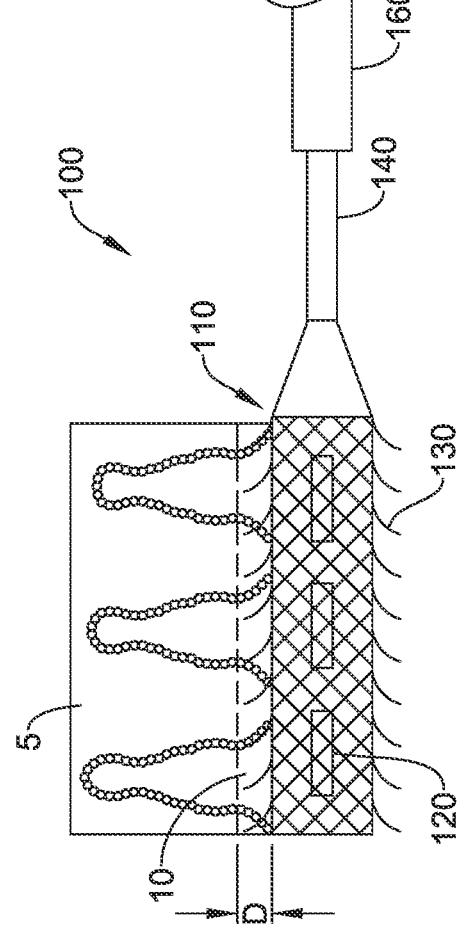
FIG. 3 is a partial cross-sectional view of the resurfacing device of FIG. 1 in position adjacent a target tissue site.

FIG. 3 illustrates a method of resurfacing tissue. The catheter shaft 140 is advanced into contact with tissue at the treatment target site, for example within the duodenum. The scaffold 110 is in the unexpanded configuration. When the resurfacing device 100 reaches the treatment target site, the scaffold 110 is expanded. For a self-expanding scaffold 110, an outer sheath 160 is withdrawn proximally, allowing the scaffold 110 to expand, which places the electrodes 120 and debridement elements 130 in contact with the duodenal wall 5. The electrodes 120 are activated to ablate a shallow layer of diseased cells 10. The ablation depth D may be adjusted by varying the energy delivered by the electrodes 120. In some examples, the ablation depth D may be from 10-700 μm. The average duodenal mucosa depth including crypt depth, mucosa and submucosa can range from 10-700 μm. The ablation depth may be selected based on the depth of diseased tissue. Once the desired depth of tissue is ablated, the scaffold 110 may be rotated and/or moved axially via the catheter shaft 140 causing the debridement elements 130 to remove the ablated tissue. Once the device 100 is removed, a fresh layer of healthy tissue remains.

Figure 4:
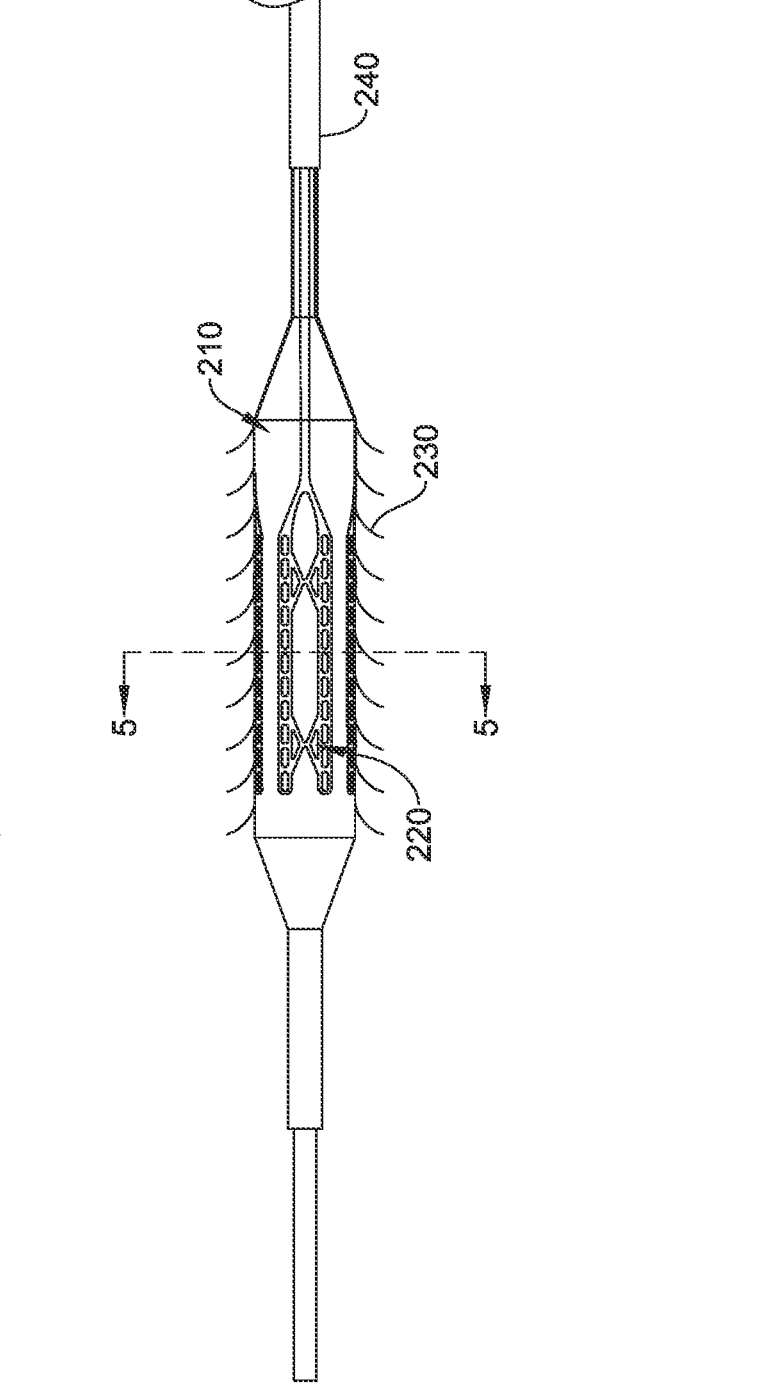
FIG. 4 is a side view of another illustrative resurfacing device.
Figure 5:
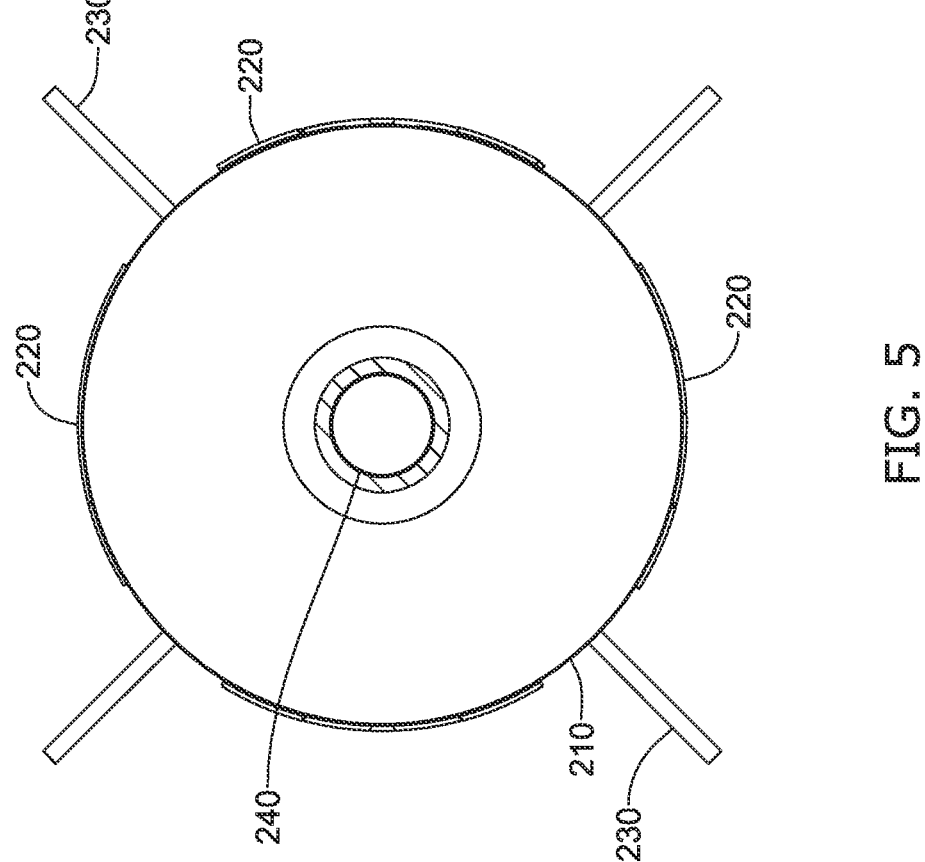
FIG. 5 is a cross-sectional view of the resurfacing device of FIG. 4 taken along line 5-5.

FIGS. 4 and 5 illustrate another embodiment of resurfacing device 200 in which the mesh scaffold has been replaced with an expandable balloon 210 attached to a catheter shaft 240. The electrodes 220 and debridement elements 230 are disposed on the outer surface of the balloon 210 and may be attached with adhesive. The arrangement, shape, and structure of the electrodes 220 and debridement elements 230 may be the same as those discussed above. In the cross-sectional view shown in FIG. 5, elongate debridement elements 230 are shown extending radially outward from the outer surface of the balloon 210, disposed between the electrodes 220. In some examples, the debridement elements 230 may be disposed circumferentially around the balloon 210, as shown in FIG. 5. In other examples, the debridement elements 230 may be disposed on only half or a fraction of the outer circumference of the balloon 210. In some examples, the balloon 210 with debridement elements 230 may be a cutting balloon such as those described in U.S. Pat. No. 8,491,615, the entire content of which is incorporated herein by reference.

Figure 6:
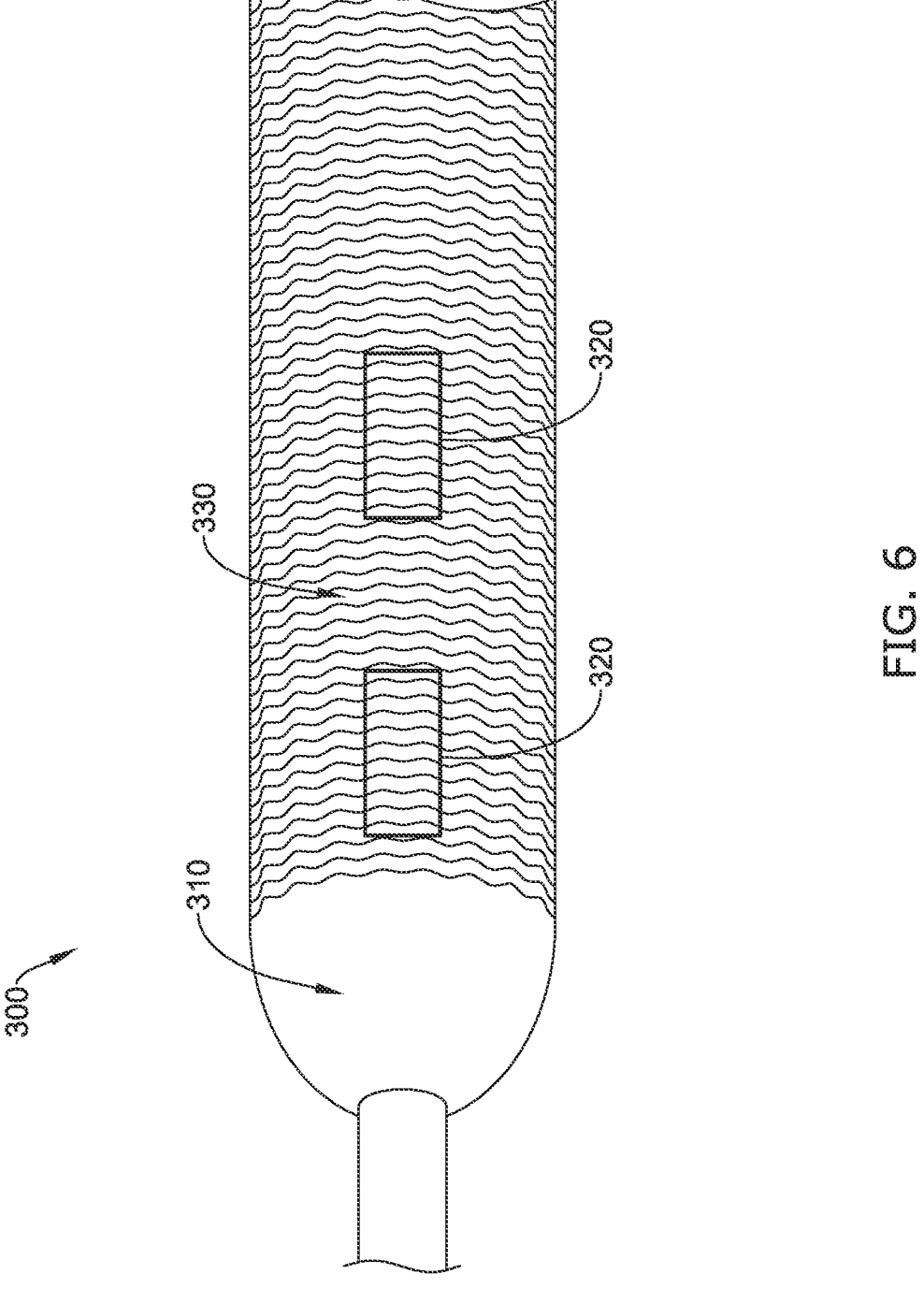
FIG. 6 is a side view of a further illustrative resurfacing device.

In a further example, illustrated in FIG. 6, the resurfacing device 300 may include a balloon 310 with a micropattern of debridement elements 330 formed on the outer surface of the balloon 310 or on a sleeve disposed over the balloon 310. At least one electrode 320 may also be disposed on the surface of the balloon 310. The electrode(s) 320 may be arranged as described above. The micropattern of debridement elements 330 may be structured as a plurality of coarse brush type projections or a rough surface such as sand paper. The micropattern of debridement elements 330 may be formed of silicone. The micropattern of debridement elements 330 provide elevated friction between the expanding balloon 310 and tissue, enough to maintain tissue apposition during ablation and debride the ablated tissue.

The materials that can be used for the various components of resurfacing device 100 and the various expandable scaffolds disclosed herein may include those commonly associated with medical devices. For simplicity purposes, the following discussion makes reference to scaffold 110 and other components of resurfacing device 100. However, this is not intended to limit the devices and methods described herein, as the discussion may be applied to other similar resurfacing devices and/or components disclosed herein.

Expandable scaffold 110 may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®), other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

Expandable scaffold 110 may be made of a shape memory polymer, examples of which include polynorbomene and copolymers of polynorbomene, blends of polybomene with KRATON® (thermoplastic elastomer) and polyethylene, styrenic block copolymer elastomers (e.g., styrene-butadiene), polymethylmethacrylate (PMMA), polyethylene, polyurethane, polyisoprene, polycaprolactone and copolymers of polycaprolactone, polylactic acid (PLA) and copolymers of polyactic acid, polyglycolic acid (PGA) and copolymers of polyglycolic acid, copolymers of PLA and PGA, polyenes, nylons, polycyclooctene (PCO), polyvinyl acetate (PVAc), polyvinylidene fluoride (PVDF), blends of polyvinyl acetate/polyvinylidine fluoride (PVAc/PVDF), blends of polymethylmethacrylate/polyvinyl acetate/polyvinylidene fluoride (PVAc/PVDF/PMMA) and polyvinylchloride (PVC) and blends and/or combinations thereof.

In at least some embodiments, portions or all of expandable scaffold 110 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of scaffold 110 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of scaffold 110 to achieve the same result.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A resurfacing device comprising:
a catheter shaft;
an expandable scaffold attached to the catheter shaft;
at least one electrode disposed on the expandable scaffold; and
a plurality of debridement elements disposed on an outer surface of the expandable scaffold;
wherein the debridement elements are elongate members each having a first end attached to the scaffold, and a second, free end extending radially away from the scaffold and extending towards a distal end of the scaffold from the first end.

2. The device of claim 1, wherein the scaffold is self-expandable.

3. The device of claim 2, wherein the scaffold is a shape memory stent.

4. The device of claim 1, wherein the elongate members are metal blades.

5. The device of claim 1, wherein the at least one electrode includes at least first and second electrodes aligned longitudinally along a single axis along the scaffold.

6. The device of claim 1, wherein the at least one electrode includes at least first and second electrodes aligned circumferentially around the scaffold.

7. The device of claim 1, wherein the at least one electrode is a radiofrequency electrode.

8. The device of claim 1, wherein the at least one electrode is configured for electroporation.

9. The device of claim 1, wherein the scaffold and debridement elements are a monolithic structure.

10. The device of claim 1, wherein the debridement elements are fixed to the scaffold.

11. The device of claim 1, wherein the elongate members have a compressed configuration where the elongate members are held against the outer surface of the scaffold, and an expanded configuration where the elongate members extend radially away from the outer surface of the scaffold.

12. The device of claim 1, wherein the second free end of the elongate members is blunt.

13. A resurfacing device comprising:
a catheter shaft;
a self-expandable shape memory scaffold attached to the catheter shaft;
at least one radiofrequency electrode disposed on the scaffold; and
a plurality of debridement elements disposed on an outer surface of the scaffold;
wherein the debridement elements are elongate members each having a first end attached to the scaffold, and a second, free end extending radially away from the scaffold and extending towards a distal end of the scaffold from the first end.

14. The device of claim 13, wherein the elongate members are metal blades.

15. The device of claim 13, wherein the scaffold and debridement elements are a monolithic structure.

16. The device of claim 13, wherein the debridement elements are fixed to the scaffold.

17. The device of claim 13, wherein the elongate members have a compressed configuration in which the elongate members are held against the outer surface of the scaffold, and an expanded configuration in which the elongate members extend radially away from the outer surface of the scaffold.

18. The device of claim 1, wherein the debridement elements are coarse brush-type projections biased at a predetermined angle relative to the outer surface of the scaffold.

* * * * *